United States Patent
Cho (10) Patent No.: US 9,730,273 B2
(45) Date of Patent: Aug. 8, 2017

(54) HEATER MODULE FOR HEATER OF FLUID INFUSION APPARATUS AND MANUFACTURING METHOD THEREOF

(71) Applicant: Yong Il Cho, Seoul (KR)

(72) Inventor: Yong Il Cho, Seoul (KR)

(*) Notice: Subject to any disclaimer, the term of this patent is extended or adjusted under 35 U.S.C. 154(b) by 67 days.

(21) Appl. No.: 14/382,570

(22) PCT Filed: Feb. 22, 2013

(86) PCT No.: PCT/KR2013/001422
§ 371 (c)(1),
(2) Date: Sep. 3, 2014

(87) PCT Pub. No.: WO2014/129687
PCT Pub. Date: Aug. 28, 2014

(65) Prior Publication Data
US 2015/0359041 A1    Dec. 10, 2015

(51) Int. Cl.
*H05B 3/44* (2006.01)
*H05B 3/00* (2006.01)
(Continued)

(52) U.S. Cl.
CPC .......... *H05B 3/0014* (2013.01); *A61F 7/0085* (2013.01); *A61M 5/445* (2013.01);
(Continued)

(58) Field of Classification Search
CPC .......... A61M 2205/3653; A61M 5/445; Y10T 29/49085; H05B 2203/003;
(Continued)

(56) References Cited

U.S. PATENT DOCUMENTS

| 6,608,968 B2 | 8/2003 | Bakke | |
| 7,158,719 B2 * | 1/2007 | Cassidy | A61M 5/44 392/466 |
| 2012/0330234 A1 | 12/2012 | Balluff | |

FOREIGN PATENT DOCUMENTS

| JP | 02-033999 | 2/1990 |
| JP | 07-192849 | 7/1995 |

(Continued)

OTHER PUBLICATIONS

Korean Patent Office, PCT Search Report of PCT/KR2013/001422, Nov. 18, 2013.

*Primary Examiner* — Shawntina Fuqua
(74) *Attorney, Agent, or Firm* — Lex IP Meister, PLLC.

(57) ABSTRACT

The present invention includes: a laminated structure of an insulation substrate; a resistance pattern laminated on one side of the insulation substrate with a pure metal or an alloy which is a mixture of two or more metals at a predetermined ratio and having a resistance value which is set by a pattern having a length and a cross-sectional area; a first insulator layer coated on an upper surface of the resistance pattern by a predetermined method to protect and insulate the resistance pattern; a conductor layer in which a metal material is deposited on the upper surface of the first insulator layer by a predetermined method; and a thin film protective layer deposited on the upper surface of the conductor layer to provide insulation from the conductor layer, waterproofing, corrosion resistance, and chemical resistance.

7 Claims, 6 Drawing Sheets

(51) Int. Cl.
　　*H05B 3/04*　　(2006.01)
　　*H05B 3/06*　　(2006.01)
　　*H05B 3/28*　　(2006.01)
　　*A61M 5/44*　　(2006.01)
　　*F24H 1/14*　　(2006.01)
　　*F24H 9/20*　　(2006.01)
　　*H05B 3/26*　　(2006.01)
　　*A61F 7/00*　　(2006.01)
　　*F24H 1/12*　　(2006.01)

(52) U.S. Cl.
　　CPC .............. *F24H 1/121* (2013.01); *F24H 1/142* (2013.01); *F24H 9/2028* (2013.01); *H05B 3/04* (2013.01); *H05B 3/06* (2013.01); *H05B 3/26* (2013.01); *H05B 3/28* (2013.01); *A61M 2205/3653* (2013.01); *H05B 2203/003* (2013.01); *H05B 2203/01* (2013.01); *H05B 2203/017* (2013.01); *H05B 2203/021* (2013.01); *Y10T 29/49085* (2015.01)

(58) Field of Classification Search
　　CPC ......... H05B 2203/009; H05B 2203/01; H05B 2203/013; H05B 2203/017; H05B 2203/021; H05B 3/0014; H05B 3/04; H05B 3/06; H05B 3/26; H05B 3/28; H05B 3/286; H05B 3/78; H05B 3/80; H05B 3/82; H05B 3/34; H05B 3/36; H05B 3/38; F24H 1/121; F24H 1/142; F24H 9/2028; A61F 7/0085; A61F 7/0086; A61F 7/0222; A61F 7/0215; A61F 2007/126

See application file for complete search history.

(56) References Cited

FOREIGN PATENT DOCUMENTS

| | | |
|---|---|---|
| JP | 10-134944 | 5/1998 |
| JP | 11-121908 | 4/1999 |
| JP | 2002-065853 | 3/2002 |
| JP | 2002-359059 | 12/2002 |
| JP | 2004-215758 | 8/2004 |
| JP | 2007-515748 | 6/2007 |
| JP | 2007-527495 | 9/2007 |
| KR | 10-0180910 | 5/1999 |
| KR | 10-0553129 | 2/2006 |
| KR | 10-0577406 | 5/2006 |
| KR | 10-0980757 | 9/2010 |
| WO | 2005/009500 | 2/2005 |
| WO | 2005/065193 | 7/2005 |
| WO | 2008-111084 | 9/2008 |

\* cited by examiner

HEATER MODULE FOR HEATER OF FLUID INFUSION APPARATUS AND MANUFACTURING METHOD THEREOF

TECHNICAL FIELD

The present invention relates to a heater module for a heater that is installed on a fluid infusion apparatus to directly heat a fluid or blood for a patient, and a manufacturing method thereof.

BACKGROUND ART

Generally, a fluid or blood is stored in a refrigerated or frozen state in order to prevent the fluid or the blood from being decomposed or prevent harmful substances from being generated.

Accordingly, when the fluid or the blood in a low temperature state is infused through the vein of a patient, a body temperature of the patient is lowered by the infused fluid or blood, and in severe cases, this can lead to death of the patient by raising a heart attack risk.

Particularly, in the case of a patient under general anesthesia of which the body temperature is not normally controlled, the patient feels severe cold after an operation, and cold points under skin where the fluid or the blood is infused are stimulated, and as a result, the patient may feel cold pain.

In order to overcome the problems, the fluid has been heated to a proper temperature by attaching a heating device to a fluid (blood) infusion apparatus. A heater module for a heater which is installed on the heating device of the fluid infusion apparatus to directly heat the fluid or the blood to the patient has been researched.

In the direct heating type of heater module for the heater, power consumption is low, the fluid may be rapidly heated, and the heater module needs to be manufactured with a small size and a light weight.

The well-known heater module for the heater includes an insulation substrate, a resistance pattern formed on the upper surface of the insulation substrate to have a predetermined resistance value, and a protective layer for protecting the resistance pattern on the upper surface of the resistance pattern. The heater module for the heater is disclosed in International Publication No. WO 2005/065193.

When the fluid (or the blood) is heated by the heater module in the heater having the constituent elements, a capacitance is generated in the protective layer between the resistance pattern made of metals to generate heat and the fluid (or the blood).

The generated capacitance enters a body of the patient through the fluid (blood), and when an apparatus measuring a bio-electric signal including an electrocardiogram (EGC), an electroencephalogram (EEG), and the like is installed to the patient, the capacitance entering the body of the patient through the fluid (blood) acts as noise with respect to a measuring signal of the apparatus measuring the bio-electric signal.

Since the noise makes it difficult to normally measure the bio-electric signal, it can lead to serious problems in determining the condition of the patient.

The above information disclosed in this Background section is only for enhancement of understanding of the background of the invention and therefore it may contain information that does not form the prior art that is already known in this country to a person of ordinary skill in the art.

DISCLOSURE

Technical Problem

The present invention has been made in an effort to provide a heater module for a heater of a fluid infusion apparatus and a manufacturing method thereof having advantages of accurately measuring a signal in an apparatus for measuring a bio-electric signal.

Technical Solution

An exemplary embodiment of the present invention provides a heater module for a heater of a fluid infusion apparatus, including: a laminated structure of an insulation substrate; a resistance pattern laminated on one side of the insulation substrate with a pure metal or an alloy which is a mixture of two or more metals at a predetermined ratio and having a resistance value which is set by a pattern having a length and a cross-sectional area; a first insulator layer coated on an upper surface of the resistance pattern by a predetermined method to protect and insulate the resistance pattern; a conductor layer in which a metal material is deposited on the upper surface of the first insulator layer by the predetermined method; and a thin film protective layer deposited on the upper surface of the conductor layer to provide insulation from the conductor layer, waterproofing, corrosion resistance, and chemical resistance.

The resistance pattern may operate as a heating element generating a heat quantity according to a predetermined resistance value when power is supplied.

A part of a ground constituted in the resistance pattern may be exposed as it is by masking in the coating of the first insulator layer, and the conductor layer deposited on the upper surface of the first insulator layer may electrically contact the exposed ground.

Another exemplary embodiment of the present invention provides a manufacturing method of a heater module for a heater of a fluid infusion apparatus, the method including: forming a thin metal sheet by coating a pure metal or an alloy thereof on one side or two sides of an insulation substrate by a predetermined method; seating a mask for forming a resistance pattern having a predetermined heating amount on the upper surface of the thin metal sheet; corroding a metal portion other than a portion with a mask pattern by exposing the thin metal sheet on which the mask is seated in a chemical material for a predetermined time; exposing the resistance pattern, an installation position of a temperature sensor, and a ground port by removing the mask and then washing with pure water and coating a first insulator on the upper surface of the resistance pattern for insulation of the resistance pattern; installing a temperature sensor by soldering and depositing a conductor made of a metal material on the upper surface of the first insulator; and depositing a thin film protective layer on the upper surface of the conductor for electrically insulating the conductor from the outside, waterproofing, corrosion resistance, and chemical resistance.

In the mask, a resistance pattern setting a resistance value required for heating by a length and a cross-sectional area of a metal foil, a power supply terminal, a measuring terminal, an installation position of a temperature sensor for measuring a temperature of the heated fluid or blood, and an exposed ground may be formed as patterns.

During the coating of the first insulator, at the ground port and the installation position of the temperature sensor, the first insulator may not be coated but is exposed by masking, and during the depositing of the conductor, the exposed ground port and the conductor may electrically contact each other.

Yet another exemplary embodiment of the present invention provides a heater module for a heater of a fluid infusion apparatus, including: a laminated structure of an insulation substrate; a heating layer generating a predetermined heating amount according to a supply of power in which a metal body is set on the insulation substrate as a pattern; a first insulator layer coated on an upper surface of the heating layer to insulate the heating layer; a conductor layer made of a metal material deposited on the upper surface of the first insulator layer to be electrically connected with a ground formed on the heating layer; a second insulator layer deposited on the upper surface of the conductor layer to insulate the conductor layer; and a thin film protective layer deposited on the upper surface of the second insulator layer to provide insulation, waterproofing, corrosion resistance, and chemical resistance.

Still another exemplary embodiment of the present invention provides a manufacturing method of a heater module, the method including: forming a thin metal sheet by coating a metal body on one side or two sides of an insulation substrate; seating a mask for forming a resistance pattern having a predetermined resistance amount on the upper surface of the thin metal sheet; corroding a metal portion other than a portion with a mask pattern by exposing the thin metal sheet on which the mask is seated in a chemical material for a predetermined time; exposing the resistance pattern, an installation position of a temperature sensor, and a ground port by removing the mask and then washing with pure water and coating a first insulator on the upper surface of the resistance pattern; electrically connecting the exposed ground port and the conductor by installing a temperature sensor at an installation position of the temperature sensor by soldering and depositing a conductor made of a metal material on the upper surface of the first insulator; electrically insulating the conductor by coating a second insulator on the upper surface of the conductor; and depositing a thin film protective layer on the upper surface of the second insulator.

Advantageous Effect

According to the exemplary embodiment of the present invention, since a capacitance generated in a heater module of a heater may flow out to a ground through a conductor layer, when a signal is measured in the EGC and the EEC, noise inflow of the capacitance may be blocked, and as a result, more accurate measurement is possible.

MODE FOR INVENTION

As those skilled in the art would realize, the described embodiments may be modified in various different ways, all without departing from the spirit or scope of the present invention. Accordingly, the drawings and description are to be regarded as illustrative in nature and not restrictive.

Figure 1:
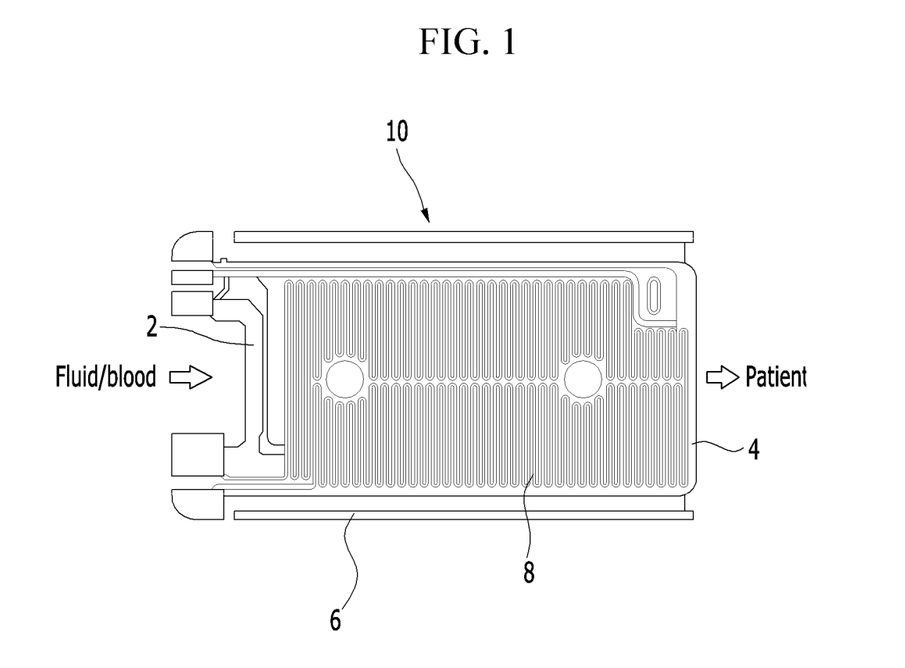
FIG. 1 is a schematic diagram of a heating device of a fluid infusion apparatus according to the present invention.

FIG. 1 schematically illustrates a heating device applied to a fluid infusion apparatus. A heating device 10 includes a case 6 having an inlet 2 connected with a fluid infusion apparatus (not illustrated) to receive a fluid and an outlet 4 discharging the received fluid after it is heated. Since the case 6 may be used as a general structure, a more detailed description is omitted. A heater module 8 as a means for heating the fluid or blood to a temperature close to a body temperature of a person is provided at an inner side of the case 6.

The heater module of the present invention may be, for example, a fluid infusion system disclosed in International Publication No. WO 2005/065193. Accordingly, the detailed description of the fluid infusion system is omitted.

Figure 2:
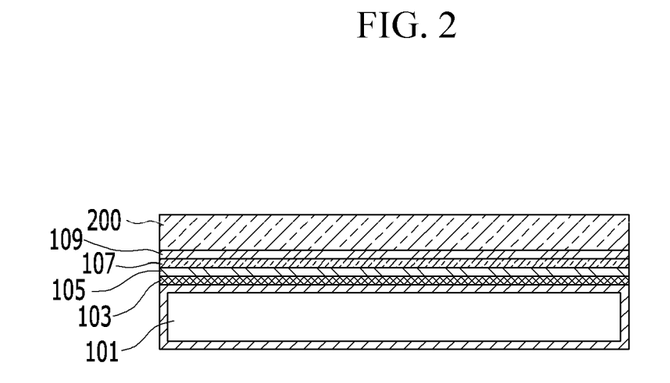
FIG. 2 is a diagram illustrating a laminated structure of a heater module for a heater according to a first exemplary embodiment of the present invention.

FIG. 2 illustrates a laminated structure of a heater module for a heater according to a first exemplary embodiment of the present invention. A heater module 8 for a heater according to the first exemplary embodiment of the present invention includes an insulation substrate 101, a resistance pattern 103 laminated on one side or two sides of the insulation substrate 101, a first insulator layer 105 laminated on an upper surface of the resistance pattern 103, a conductor layer 107 laminated on an upper surface of the first insulator layer 105, and a protective layer 109 laminated on an upper surface of the conductor layer 107.

The resistance pattern 103 laminated on one side or two sides of the insulation substrate 101 is formed to have a resistance value set by a length and a cross-sectional area, and operates as a heating element generating a heat quantity of the set resistance value when power is supplied.

The resistance pattern 103 may be constituted by pure metals including copper, iron, nickel, chromium, and the like, or alloys which are mixtures of two or more metals at a predetermined ratio.

The resistance patterns 103 are simultaneously formed on two parts of the insulation substrate 101 and electrically connected to each other by using a via hole, and as a result, a size of the insulation substrate 101 may be minimized and a heating amount may be maximally obtained.

The first insulator layer 105 is coated on the upper surface of the resistance pattern 103 by a predetermined method to protect and insulate the resistance pattern 103, and may include colors such as green or white.

The first insulator layer 105 is not coated but is exposed on a part of the ground constituted in the resistance pattern 103 by masking.

The first insulator layer 105 may include colors such as green or white for distinguishing from the resistance pattern 103.

The conductor layer 107 is coated on the upper surface of the first insulator layer 105 by a predetermined method so that the ground of the resistance pattern 103 exposed on the surface and the conductor layer 107 may naturally contact each other.

The conductor layer 107 may be made of a metallic material including aluminum, copper, and the like, and may be deposited on the upper surface of the first insulator layer 105.

The protective layer 109 is coated on the upper surface of the conductor layer 107 to stabilize the deposition of the conductor layer 107, provide an insulating property and electrical waterproofing, and provide excellent defense against chemical materials or oxidation.

The protective layer 109 is constituted by harmless materials, and is formed as a thin film protective layer.

While the fluid or blood 200 which is infused to a patient by using the heater module for the heater having the above laminated structure is heated to a body temperature, a capacitance is generated in the insulator layer 105 between the resistance pattern 103 constituted by a metal object and the conductor layer 107, and the generated capacitance flows to the ground formed on the resistance pattern 103 through the conductor layer 107.

Accordingly, since the capacitance does not flow to the human body through the fluid or the blood infused to the patient and does not influence the signals measured by the apparatus for measuring the bio-electric signal, stable and reliable measurement of the bio-electric signal is provided.

Figure 3:
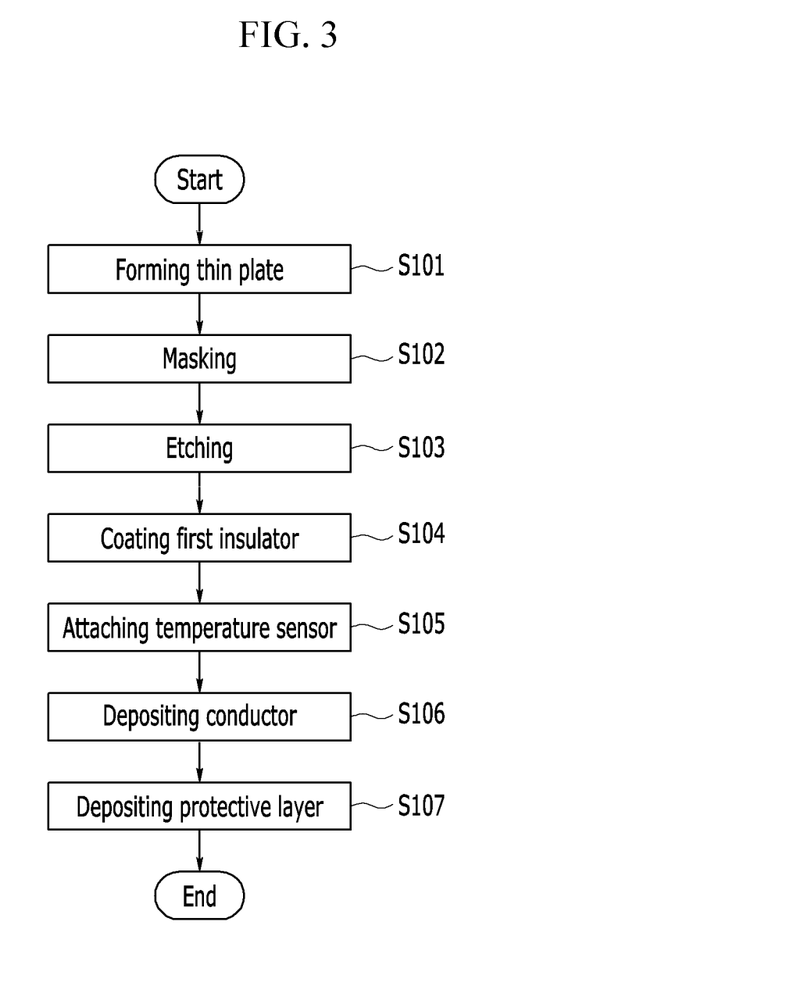
FIG. 3 is a flowchart of a manufacturing process of the heater module for the heater according to the first exemplary embodiment of the present invention.

FIG. 3 is a flowchart of a manufacturing process of the heater module for the heater according to the first exemplary embodiment of the present invention. The manufacturing process of the heater module for the heater according to the first exemplary embodiment of the present invention is performed as follows.

A thin metal sheet is formed by coating pure metals including copper, iron, nickel, chromium, and the like or alloys which are mixtures of two or more metals at a predetermined ratio on the insulation substrate 101 by a predetermined method (S101).

When the thin metal sheet is formed on one side or two sides of the insulation substrate 101 in step S101, a mask for forming the resistance pattern 103 having a predetermined resistance value is mounted on the upper surface of the thin metal sheet (S102).

Figure 6:
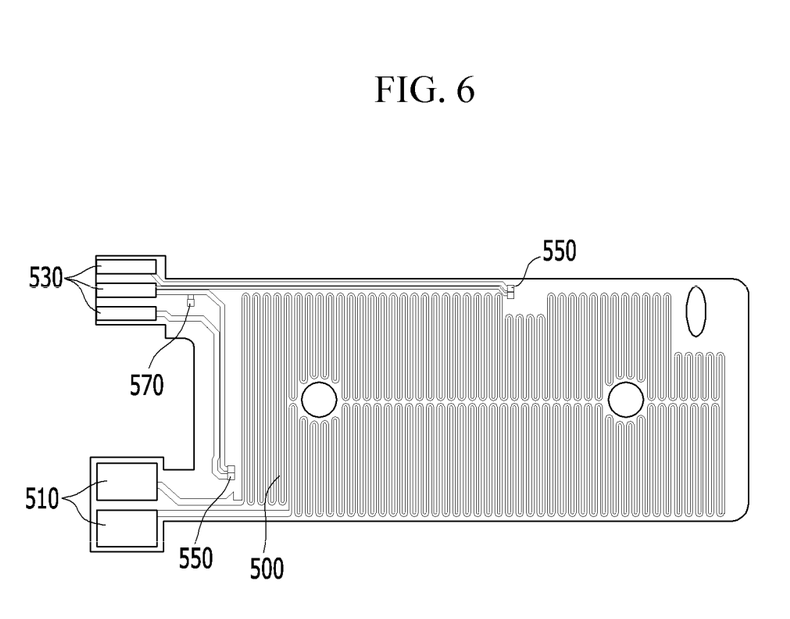
FIG. 6 is a diagram illustrating a PCB pattern of a heater module for a heater according to an exemplary embodiment of the present invention.

In the mask, as illustrated in FIG. 6, a pattern 500 which sets a resistance value required for heating by a length and a cross-sectional area of a metal foil, and patterns such as a power supply terminal 510, a measuring terminal 530, an installation position 550 of a temperature sensor for measuring a temperature of the infused fluid or blood, and an exposed ground 570 are further included.

When the seating of the mask on the upper surface of the thin metal sheet is completed in step S102, an etching process is performed by coating a chemical material such as sulfuric acid on the upper portion of the mask for a predetermined time by a predetermined method and corroding other metal portions with a mask pattern (S103).

Further, the etching process may be performed by a method in which the thin metal sheet seated with the mask is soaked in the chemical material such as sulfuric acid for a predetermined time.

When the etching process of step S103 is completed, the resistance pattern 103 having the predetermined resistance value is exposed by removing the mask and then washing with pure water, and the resistance pattern 103 is protected and electrically insulated from the outside by coating a first insulator on the upper surface of the resistance pattern 103 by the predetermined method (S104).

While the first insulator is coated on the upper surface of the resistance pattern 103, the mask is applied so that the first insulator is not coated on the installation position 550 of the temperature sensor and the exposed ground 570.

Accordingly, when the coating of the first insulator in step S104 is completed, the temperature sensor is attached at the installation position 550 of the temperature sensor by soldering, and epoxy is coated on the upper portion thereof to be insulated (S105).

When the attaching of the temperature sensor in step S105 is completed, the exposed ground 570 and the conductor may naturally electrically contact each other by depositing the conductor made of a metal material including aluminum, copper, and the like on the upper surface of the first insulator (S106).

When the depositing of the conductor in step S106 is completed, the thin film protective layer is deposited on the upper surface of the conductor with a harmless material to stabilize the deposition of the conductor and provide electrical insulation from the outside, waterproofing, and corrosion/chemical resistance (S107).

Figure 4:
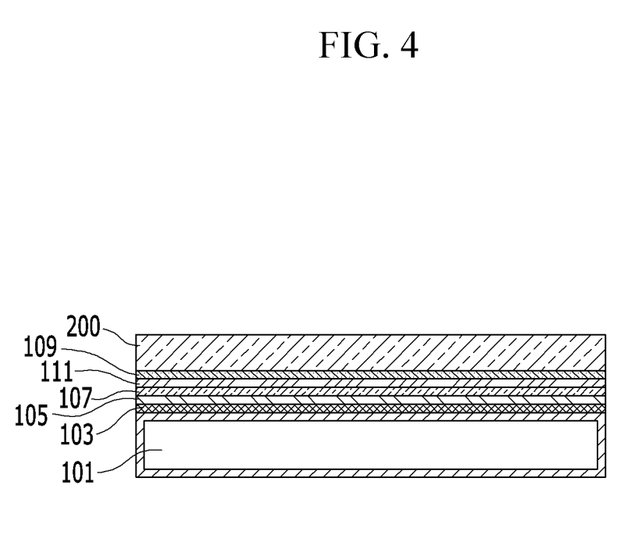
FIG. 4 is a diagram illustrating a laminated structure of a heater module for a heater according to a second exemplary embodiment of the present invention.

FIG. 4 is a diagram illustrating a laminated structure of a heater module for a heater according to a second exemplary embodiment of the present invention. In a heater module for a heater according to the second exemplary embodiment of the present invention, an insulation substrate 101 and a resistance pattern 103 on one side or two sides of the insulation substrate 101 are laminated, a first insulator layer 105 is laminated on an upper surface of the resistance pattern 103, a conductor layer 107 is laminated on an upper surface of the first insulator layer 105, a second insulator layer 111 is laminated on an upper surface of the conductor layer 107, and a protective layer 109 is laminated on an upper surface of the second insulator layer 111.

The resistance pattern 103 laminated on one side or two sides of the insulation substrate 101 is formed to have a resistance value set by a length and a cross-sectional area, and operates as a heating element generating a heat quantity of the set resistance value when power is supplied.

The resistance pattern 103 may be constituted by pure metals including copper, iron, nickel, chromium, and the like, or alloys which are mixtures of two or more metals at a predetermined ratio.

The resistance patterns 103 are simultaneously formed on the upper surface and the lower surface of the insulation substrate 101 and electrically connected to each other by using a via hole, and as a result, a size of the insulation substrate 101 may be minimized and a heating amount may be maximally obtained.

The first insulator layer 105 is coated on the upper surface of the resistance pattern 103 by a predetermined method to protect and insulate the resistance pattern 103, and may include colors such as green or white.

The first insulator layer 105 is not coated but is exposed on a part of the ground constituted in the resistance pattern 103 by masking.

The conductor layer 107 is coated on the upper surface of the first insulator layer 105 by a predetermined method so that the exposed ground of the resistance pattern 103 and the conductor layer 107 may naturally contact each other.

The conductor layer 107 may be made of a metallic material including aluminum, copper, and the like, and may be deposited on the upper surface of the first insulator layer 105.

The second insulator layer 111 is coated on the upper surface of the conductor layer 107 by a predetermined method to stabilize the deposition of the conductor layer 107 and insulate the conductive layer 107 from the outside.

The protective layer 109 is coated on the upper surface of the second insulator layer 111 to provide an insulating property from the outside and waterproofing and defense power against chemical materials or oxidation.

The protective layer 109 is constituted by harmless materials, and is formed as a thin film protective layer.

While the fluid or blood 200 which is infused to a patient by using the heater module for the heater having the above laminated structure is heated to a body temperature, a capacitance is generated in the first insulator layer 105 between the resistance pattern 103 constituted by a metal object and the conductor layer 107, and the generated capacitance flows to the ground formed on the resistance pattern 103 through the conductor layer 107.

Accordingly, since the capacitance does not flow to the human body through the fluid or the blood infused to the patient and does not influence the signals measured in the apparatus for measuring the bio-electric signal, the stable and reliable measurement of the bio-electric signal is provided.

Figure 5:
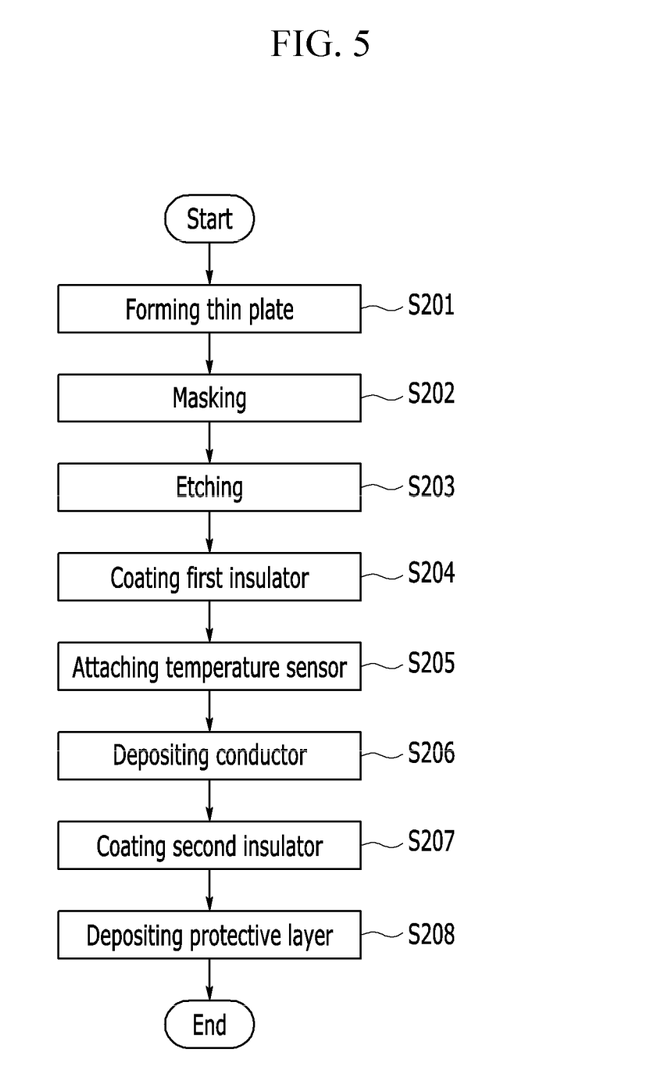
FIG. 5 is a flowchart of a manufacturing process of the heater module for the heater according to the second exemplary embodiment of the present invention.

FIG. 5 is a flowchart of a manufacturing process of the heater module for the heater according to the second exemplary embodiment of the present invention. The manufacturing process of the heater module for the heater according to the second exemplary embodiment of the present invention is performed as follows.

A thin metal sheet is formed by coating pure metals including copper, iron, nickel, chromium, and the like or alloys which are mixtures of two or more metals at a predetermined ratio on one side or two sides of the insulation substrate 101 by a predetermined method (S201).

When the thin metal sheet is formed on one side or two sides of the insulation substrate 101 in step S201, a mask for forming the resistance pattern 103 having a predetermined resistance value is mounted on the upper surface of the thin metal sheet (S202).

In the mask, as illustrated in FIG. 6, a pattern 500 which sets a resistance value required for heating by a length and a cross-sectional area of a metal foil, and patterns such as a power supply terminal 510, a measuring terminal 530, an installation position 550 of a temperature sensor for measuring a temperature of the infused fluid or blood, and an exposed ground 570 are further included.

When the seating of the mask on the upper surface of the thin metal sheet is completed in step S202, an etching process is performed by coating a chemical material such as sulfuric acid on the upper portion of the mask for a predetermined time by a predetermined method and corroding other metal portions with a mask pattern (S203).

Further, the etching process may be performed by a method in which the thin metal sheet seated with the mask is soaked in the chemical material such as sulfuric acid for a predetermined time.

When the etching process in step S203 is completed, the resistance pattern 103 having the predetermined resistance value is exposed by removing the mask and then washing with pure water, and the resistance pattern 103 is protected and electrically insulated from the outside by coating a first insulator on the upper surface of the resistance pattern 103 by the predetermined method (S204).

While the first insulator is coated on the upper surface of the resistance pattern 103, the mask is applied so that the first insulator is not coated on the installation position 550 of the temperature sensor and the exposed ground 570.

Accordingly, when the coating of the first insulator in step S204 is completed, the temperature sensor is attached to the installation position 550 of the temperature sensor by soldering, and epoxy is coated on the upper portion thereof to be insulated (S205).

When the attaching of the temperature sensor in step S205 is completed, the exposed ground 570 and the deposited conductor may naturally contact each other by depositing the conductor 107 made of a metal material including aluminum, copper, and the like on the upper surface of the first insulator (S206).

When the depositing of the conductor in step S206 is completed, a second insulator is coated on the upper surface of the conductor by a predetermined method to insulate the conductor from the outside (S207).

When the coating of the second insulator in step S207 is completed, the thin film protective layer (protective film) is deposited on the upper surface of the second insulator with a harmless material to provide electrical insulation from the outside, waterproofing, and corrosion/chemical resistance (S208).

When the heater modules for the heater having the laminated structures of the first exemplary embodiment and the second exemplary embodiment and the apparatus for measuring the bio-electric signal are simultaneously used, it is verified that the measured bio-electric signal is detected in a stable state without generating distortion of a waveform.

That is, while the fluid or blood which is infused to a patient by using the heater module for the heater having the above laminated structure is heated, a capacitance which is generated in the insulator layer between the resistance pattern constituted by a metal object and the conductor layer flows to the ground formed on the resistance pattern through the insulator layer.

Accordingly, since the capacitance does not flow to the human body through the fluid or the blood infused to the patient and does not influence the signals measured in the apparatus for measuring the bio-electric signal, stable and reliable measurement of the bio-electric signal is provided.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A heater module for a heater of a fluid infusion apparatus, comprising:
   a laminated structure of an insulation substrate;
   a resistance pattern laminated on one side of the insulation substrate with a pure metal or an alloy which is a mixture of two or more metals at a predetermined ratio and having a resistance value which is set by a pattern having a length and a cross-sectional area; and
   a first insulator layer coated on an upper surface of the resistance pattern by a predetermined method to protect and insulate the resistance pattern; and
   a conductor layer in which a metal material is deposited on the upper surface of the first insulator layer by a predetermined method; and
   a thin film protective layer deposited on the upper surface of the conductor layer to provide insulation from the conductor layer, waterproofing, corrosion resistance, and chemical resistance,
   wherein a part of a ground formed in the resistance pattern by masking in the coating of the first insulator layer is exposed, and the conductor layer deposited on the upper surface of the first insulator layer electrically contacts the part of the ground which is exposed.

2. The heater module of claim 1, wherein the resistance pattern operates as a heating element generating a heat quantity according to a predetermined resistance value when power is supplied.

3. A manufacturing method of a heater module for a heater of a fluid infusion apparatus, the method comprising:
forming a thin metal sheet by coating a pure metal or an alloy thereof on one side or two sides of an insulation substrate by a predetermined method;
seating a mask for forming a resistance pattern having a predetermined heating amount on the upper surface of the thin metal sheet;
corroding a metal portion other than a portion with a mask pattern by exposing the thin metal sheet on which the mask is seated to a chemical material for a predetermined time;
exposing the resistance pattern, an installation position of a temperature sensor, and a ground port by removing the mask and then washing with pure water and coating a first insulator on the upper surface of the resistance pattern for insulation of the resistance pattern;
installing a temperature sensor by soldering and depositing a conductor made of a metal material on the upper surface of the first insulator; and
depositing a thin film protective layer on the upper surface of the conductor for electrically insulating the conductor from the outside, waterproofing, corrosion resistance, and chemical resistance.

4. The manufacturing method of claim 3, wherein in the mask, a resistance pattern setting a resistance value required for heating by a length and a cross-sectional area of a metal foil, a power supply terminal, a measuring terminal, an installation position of a temperature sensor for measuring a temperature of the heated fluid or blood, and an exposed ground are formed as patterns.

5. The manufacturing method of claim 3, wherein:
during the coating of the first insulator, at the ground port and the installation position of the temperature sensor, the insulator is not coated but is exposed by masking, and
during the depositing of the conductor, the exposed ground port and the conductor electrically contact each other.

6. A heater module for a heater of a fluid infusion apparatus, comprising:
an insulation substrate;
a heating layer generating a predetermined heating amount according to a supply of power in which a metal body is set on the insulation substrate as a pattern;
a first insulator layer coated on an upper surface of the heating layer to insulate the heating layer;
a conductor layer deposited on the upper surface of the first insulator layer to be electrically connected with a ground formed on the heating layer and made of a metal material;
a second insulator layer deposited on the upper surface of the conductor layer to insulate the conductor layer; and
a thin film protective layer deposited on the upper surface of the second insulator layer to provide insulation, waterproofing, corrosion resistance, and chemical resistance.

7. A manufacturing method of a heater module for a heater of a fluid infusion apparatus, the method comprising:
forming a thin metal sheet by coating a metal body on one side or two sides of an insulation substrate;
seating a mask for forming a resistance pattern having a predetermined resistance amount on the upper surface of the thin metal sheet;
corroding a metal portion other than a portion with a mask pattern by exposing the thin metal sheet on which the mask is seated in a chemical material for a predetermined time;
exposing the resistance pattern, an installation position of a temperature sensor, and a ground port by removing the mask and then washing with pure water and coating a first insulator on the upper surface of the resistance pattern;
electrically connecting the exposed ground port and the conductor by installing a temperature sensor at an installation position of the temperature sensor by soldering and depositing a conductor made of a metal material on the upper surface of the first insulator;
electrically insulating the conductor by coating a second insulator on the upper surface of the conductor; and
depositing a thin film protective layer on the upper surface of the second insulator.

* * * * *